US012653490B2

(12) United States Patent
Tek et al.

(10) Patent No.: US 12,653,490 B2
(45) Date of Patent: Jun. 16, 2026

(54) CARDIAC FLOW DETECTION BASED ON MORPHOLOGICAL MODELING IN MEDICAL DIAGNOSTIC ULTRASOUND IMAGING

(71) Applicant: Siemens Medical Solutions USA, Inc., Malvern, PA (US)

(72) Inventors: Huseyin Tek, Princeton, NJ (US); Bogdan Georgescu, Princeton, NJ (US); Tommaso Mansi, Plainsboro, NJ (US); Frank Sauer, Princeton, NJ (US); Dorin Comaniciu, Princeton, NJ (US); Helene C. Houle, San Jose, CA (US); Ingmar Voigt, Erlangen (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 19/219,031

(22) Filed: May 27, 2025

(65) Prior Publication Data

US 2025/0281146 A1 Sep. 11, 2025

Related U.S. Application Data

(62) Division of application No. 17/531,980, filed on Nov. 22, 2021, now Pat. No. 12,329,565, which is a
(Continued)

(51) Int. Cl.
*A61B 8/00* (2006.01)
*A61B 8/06* (2006.01)
(Continued)

(52) U.S. Cl.
CPC ............... *A61B 8/065* (2013.01); *A61B 8/06* (2013.01); *A61B 8/0883* (2013.01);
(Continued)

(58) Field of Classification Search
CPC ......... A61B 8/065; A61B 8/06; A61B 8/0883; A61B 8/0891; A61B 8/463; A61B 8/465; A61B 8/466; A61B 8/469; A61B 8/483; A61B 8/488; A61B 8/5207; A61B 8/5223; A61B 8/5292; A61B 8/468; A61B 8/5246;
(Continued)

(56) References Cited

U.S. PATENT DOCUMENTS 7,153,268 B2 12/2006 Li et al.
7,288,068 B2 10/2007 Bakircioglu et al.
(Continued)

FOREIGN PATENT DOCUMENTS

WO 2015191414 A2 12/2015

OTHER PUBLICATIONS

Berne & Levy Physiology, 6th edition. 2008. pp. 322-324 (Year: 2008).
(Continued)

*Primary Examiner* — Amal Aly Farag

(57) ABSTRACT

For cardiac flow detection in echocardiography, by detecting one or more valves, sampling planes or flow regions spaced from the valve and/or based on multiple valves are identified. A confidence of the detection may be used to indicate confidence of calculated quantities and/or to place the sampling planes.

20 Claims, 3 Drawing Sheets

30 — Scan with Ultrasound

32 — Detect One or more Valves

34 — Determine Confidence

36 — Place Measurement Area or Region Based on Valve Location

38 — Refine Measurement Area or Region

40 — Calculate Cardiac Flow for Area or Region

42 — Output Image or Quantity

Related U.S. Application Data division of application No. 15/797,161, filed on Oct. 30, 2017, now abandoned.

(51) Int. Cl.

| | |
|---|---|
| *A61B 8/08* | (2006.01) |
| *G06T 7/00* | (2017.01) |
| *G16H 50/20* | (2018.01) |

(52) U.S. Cl.
CPC ............ *A61B 8/0891* (2013.01); *A61B 8/463* (2013.01); *A61B 8/465* (2013.01); *A61B 8/466* (2013.01); *A61B 8/469* (2013.01); *A61B 8/483* (2013.01); *A61B 8/488* (2013.01); *A61B 8/5207* (2013.01); *A61B 8/5223* (2013.01); *A61B 8/5292* (2013.01); *G06T 7/0012* (2013.01); *G16H 50/20* (2018.01); *A61B 8/468* (2013.01); *A61B 8/5246* (2013.01); *G06T 2207/10132* (2013.01); *G06T 2207/30048* (2013.01); *G06T 2207/30104* (2013.01); *G06V 2201/031* (2022.01)

(58) Field of Classification Search
CPC ......... G06T 7/0012; G06T 2207/10132; G06T 2207/30048; G06T 2207/30104; G16H 50/20; G16H 30/40; G06V 2201/031
See application file for complete search history.

(56) References Cited

U.S. PATENT DOCUMENTS

| | | | |
|---|---|---|---|
| 8,771,189 B2 | 7/2014 | Ionasec et al. | |
| 9,033,887 B2 | 5/2015 | Ionasec et al. | |
| 10,271,817 B2 | 4/2019 | Voigt et al. | |
| 2007/0167794 A1 | 7/2007 | Dala-Krishna | |
| 2007/0255136 A1 | 11/2007 | Kristofferson et al. | |
| 2008/0183232 A1 | 7/2008 | Voss et al. | |
| 2010/0240996 A1 | 9/2010 | Ionasec et al. | |
| 2012/0041313 A1 | 2/2012 | Tanaka et al. | |
| 2013/0144161 A1 | 6/2013 | Wang et al. | |
| 2014/0052001 A1* | 2/2014 | Ionasec ................ | A61B 5/7264 |
| | | | 600/440 |
| 2015/0366532 A1 | 12/2015 | Voigt et al. | |
| 2016/0228190 A1* | 8/2016 | Georgescu ............ | A61B 34/10 |

OTHER PUBLICATIONS

Burlina, Philippe, et al. "Patient-Specific Modeling and Analysis of the Mitral Valve Using 3D-TEE." IPCAI. 2010.

Grady, Leo, et al. "Regurgitation quantification using 3D PISA in volume echocardiography." International Conference on Medical Image Computing and Computer-Assisted Intervention. Springer, Berlin, Heidelberg, 2011.

Ionasec, Razvan Ioan, et al. "Patient-specific modeling and quantification of the aortic and mitral valves from 4-D cardiac CT and Tee." IEEE transactions on medical imaging 29.9 (2010): 1636-1651.

Mahmood, Feroze, et al. "Intraoperative application of geometric three-dimensional mitral valve assessment package: a feasibility study." Journal of cardiothoracic and vascular anesthesia 22.2 (2008): 292-298.

Mansi, Tommaso, et al. "Towards patient-specific finite-element simulation of MitralClip procedure." International Conference on Medical Image Computing and Computer-Assisted Intervention. Springer, Berlin, Heidelberg, 2011.

Plicht, Björn, et al. "Direct quantification of mitral regurgitant flow volume by real-time three-dimensional echocardiography using dealiasing of color Doppler flow at the vena contracta." Journal of the American Society of Echocardiography 21.12 (2008): 1337-1346.

Schneider, Robert J., et al. "Patient-specific mitral leaflet segmentation from 4D ultrasound." International Conference on Medical Image Computing and Computer-Assisted Intervention. Springer, Berlin, Heidelberg, 2011.

Skaug, Thomas R., et al. "Quantification of mitral regurgitation using high pulse repetition frequency three-dimensional color Doppler." Journal of the American Society of Echocardiography 23.1 (2010): 1-8.

Veronesi, F., et al. "Semi-automatic tracking for mitral annulus dynamic analysis using real-time 3D echocardiography." Computers in Cardiology, 2006. IEEE, 2006.

Wenk, Jonathan F., et al. "First finite element model of the left ventricle with mitral valve: insights into ischemic mitral regurgitation." The Annals of thoracic surgery 89.5 (2010): 1546-1553.

Yosefy, Chaim, et al. "Proximal flow convergence region as assessed by real-time 3-dimensional echocardiography: challenging the hemispheric assumption." Journal of the American Society of Echocardiography 20.4 (2007): 389-396.

Zhu, Yun, et al. "A dynamical shape prior for LV segmentation from RT3D echocardiography." International Conference on Medical Image Computing and Computer-Assisted Intervention. Springer, Berlin, Heidelberg, 2009.

* cited by examiner

30 — Scan with Ultrasound

32 — Detect One or more Valves

34 — Determine Confidence

36 — Place Measurement Area or Region Based on Valve Location

38 — Refine Measurement Area or Region

40 — Calculate Cardiac Flow for Area or Region

42 — Output Image or Quantity

Global Valve Position Estimation

Sampling Plane from Valve Detector

CARDIAC FLOW DETECTION BASED ON MORPHOLOGICAL MODELING IN MEDICAL DIAGNOSTIC ULTRASOUND IMAGING

PRIORITY CLAIM

This application is a divisional of and claims priority to U.S. patent application Ser. No. 17/531,980 filed Nov. 22, 2021, which is a divisional of and claims priority to U.S. patent application Ser. No. 15/797,161, filed Oct. 30, 2017, both of which are entirely incorporated by reference.

BACKGROUND

The present embodiments relate to cardiac flow detection in medical diagnostic ultrasound imaging.

The quantification of flow volume is important for evaluation of patients with cardiac dysfunction and cardiovascular disease. Intracardiac blood flow is important for assessment of cardiac function, for estimation of shunt flows in congenital cardiac defects, and for assessment of regurgitation in the presence of valvular disease.

Accurate flow quantification remains a significant challenge for cardiologists. For assessing valve competency, both anatomy and blood flow is derived from B-mode and color Doppler three-dimensional ultrasound imaging over time (3D B/C+t). Valves are automatically detected (i.e. localized within ultrasound data) and modeled in terms of anatomical components (leaflets, annulus, root). The valve dynamics over time as well as regurgitant flow may be calculated. In this valve-specific approach, flow in other cardiac regions is not assessed quantitatively as the focus is on the most relevant transvalvular flow.

Various approaches have been used for quantifying cardiac performance. Classic approaches require extensive manual input, such as tracing an area or volume, for example, in order to compute measurements like stroke volume, ejection fraction, or cardiac output. Quantifying transvalvular blood flow directly provides additional cues via the flow over time. In addition, 3D flow quantification is potentially more accurate, as blood flow intensity may spatially vary. For quantifying ventricular inflow and outflow with 3D B/C+t, the flow sampling locations, such as the mitral annulus and the left ventricular outflow tract (LVOT) (in case of the left ventricle), are initialized by a user placing a disk-shaped sampling plane, that is parameterized by a user-defined seed point in an image as well as an orientation and a radius. The manually defined sampling locations may be tracked through a sequence of frames spanning one or more cardiac cycle(s), and the tracked locations are used compute the flow volume from aggregated color Doppler values. The manual selection or initialization of the sampling locations however leads to undesired variability and could result in inclusion of undesired flow. Even with accurate placement and tracking, the ultrasound data may not include all the desired anatomy in the field of view (e.g., due to poorly defined borders that are not well visible), resulting in inaccuracies in the calculation of the cardiac flow.

SUMMARY

By way of introduction, the preferred embodiments described below include methods, computer readable media, and systems for cardiac flow detection in echocardiography. By detecting one or more valves, sampling planes or flow regions spaced from the valve and/or based on multiple valves are identified. The use of valve detection may be similarly applied to sampling at other organs, for instance for quantifying flow through vascular structures (e.g. across stenoses). A confidence of the detection may be used to indicate confidence of calculated quantities and/or the actual presence of the valve and thus to decide whether or not to place the sampling planes.

In a first aspect, a system for detecting cardiac flow is provided, the system comprising: an ultrasound scanner configured to scan a heart volume of a patient, the scan providing B-mode and Doppler flow data; an image processor configured to detect two or more heart valves over time in the B-mode data, fit a model of the two or more heart valves to the patient using the B-mode data and a machine-learnt classifier, determine, with the machine-learnt classifier, a confidence value indicating an accuracy of the detection of the two or more heart valves in the model, place a first sampling plane for a first heart valve of the two or more heart valves and a second sampling plane for a second heart valve of the two or more heart valves based on the model, and track the first and second sampling planes over time, the image processor further configured to calculate the cardiac flow from the Doppler flow data for the first and second sampling planes over time; and a display configured to generate a visualization of the model over time as fit to the B-mode data, highlight the cardiac flow area, and indicate a value of the calculated cardiac flow.

In a second aspect, a system for detecting cardiac flow is provided, the system comprising: a transducer positioned on the chest of a patient such that acoustic energy passes between ribs of the patient to scan a heart or portion of the heart generating B-mode and Doppler flow data; and an image processor configured to detect two or more heart valves over time in the B-mode data, fit a model of the two or more heart valves to the patient using the B-mode data and a machine-learnt classifier, determine, with the machine-learnt classifier, a confidence value indicating an accuracy of the detection of the two or more heart valves in the model, place a first sampling plane for a first heart valve of the two or more heart valves and a second sampling plane for a second heart valve of the two or more heart valves based on the model, and track the first and second sampling planes over time, the image processor further configured to calculate the cardiac flow from the Doppler flow data for the first and second sampling planes over time.

In a third aspect, a system for detecting cardiac flow is provided, the system comprising: an ultrasound scanner configured to scan a heart volume of a patient over at least a heart cycle to acquire one or more volumetric ultrasound scans including B-mode and Doppler flow data; an image processor configured to detect two or more heart valves over time from the B-mode data of the one or more volumetric ultrasound scans, wherein detecting comprises detecting with a machine-learnt classifier, the image processor configured to fit a patient specific valve model to the detected two or more heart valves, determine a confidence value indicating an accuracy of the detecting of the mitral annulus and the left ventricle outflow tract in the fit patient specific valve model two or more heart valves, wherein determining the confidence comprises determining the confidence with the machine-learnt classifier, place a first sampling plane for the mitral annulus and a second sampling plane for the left ventricle outflow tract one or more sampling planes based on the fit patient specific valve model two or more heart valves, track the one or more first and second sampling planes over time based on optical flow, boundary detection, and motion prior; calculate a cardiac flow value from flow data of the volumetric ultrasound scans for the one or more first and second sampling planes over time, the calculating of the cardiac flow value limited to avoid flow during a portion of a heart cycle, and output an image of the cardiac flow value, wherein the image indicates the confidence value for the one or more first and second sampling planes.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION

Figure 1:
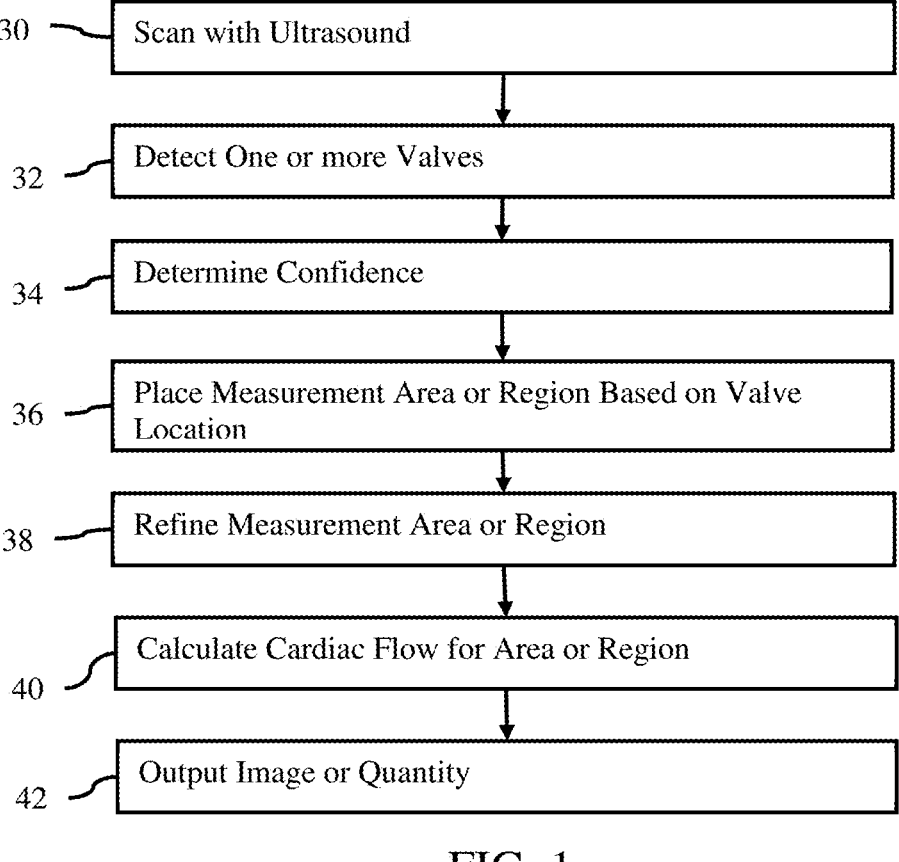
FIG. 1 is a flow chart diagram of one embodiment of a method for detecting cardiac flow in echocardiography.

Valve detectors are used for automatic cardiac flow detection. The position of flow sampling planes is automatically determined based on detection of one or more valves. There will be no need for the manual seed placement, which can be time-consuming and user-dependent. Valve detectors automatically define the measurement plane for flow calculation at one or several frames (tracking).

In one embodiment, models of both mitral and aortic valve models are used to estimate both the mitral and LVOT flow. The models are estimated based on 3D+t B-mode and color Doppler data for a single or multiple heart beats. Valve modeling uses volumetric B-mode data combined with color flow data for the estimation of a flow sampling location on a single frame. The sampling plane or planes are initialized from the valve detectors. The flow sampling locations are tracked over time by fusing information from multiple cues, such as optical flow, boundary detection, and motion prior. Automated flow measurements are performed using the 3D+t color Doppler data to quantify stroke volume, inflow, outflow, and/or regurgitant flow.

In another embodiment, 3D B-mode and color Doppler images of the heart are acquiring with transesophageal (TEE) or transthoracic (TTE) echocardiography. By combining both B-Mode and color flow, the valve anatomy is accurately modeled. The anatomy global position is localized from valve detectors. Sampling planes are initialized from the valve detectors, such as the anatomy global position, on a single frame. The sampling planes are tracked over time for automated quantification of flow measurements, which are displayed to assist in diagnosis.

A 2-step process first determines morphological and timing information from real-time, volumetric ultrasound data acquired in B-mode and color Doppler mode (B+Color). In a second act, the flow information contained in the same data set is analyzed and interpreted considering the geometric (morphological) and timing information to automatically quantify volumetric flow through anatomical structures, such as heart valves or vessels, and to compute parameters like cardiac output and regurgitant volume and/or fraction. Pressure gradients may also be quantified given echocardiography with a high pulse repetition frequency for 3D scanning for quantifying high velocity flows. In addition to identifying the anatomical structures, such as heart valves or vessels or pathological deformations such as vascular stenosis, to compute the flow through the valve, vessel and/or stenosis, the geometric, timing and flow information are used to (1) determine whether flow information can be quantified with high confidence given the completeness and quality of the data and to (2) correct for artifacts that arise from shortcomings in the flow measurements with ultrasound given the detected geometry.

A single holistic and consistent workflow may be applied for both TTE and TEE throughout the whole clinical workflow. In diagnosis and monitoring, TTE is used for early detection and intervention decisions. For intervention and follow up, pre, intra, or post (e.g., immediate) operative TEE examinations support assessment of outcome and decisions for additional measures. Intracardiac catheter echocardiography (ICE) may be used for assessment or during intervention. These assessments, regardless of the type of transducer or heart scan, are supported quantitatively and qualitatively. Overall cardiac performance based on detection of the valve or valves is indicated by integrating any biomarkers.

FIG. 1 shows one embodiment of a method for detecting cardiac flow in echocardiography. The method is implemented by a medical diagnostic ultrasound imaging system, a review station, a workstation, a computer, a Picture Archiving and Communication System (PACS) station, a server, combinations thereof, or other device for image processing medical diagnostic ultrasound data. For example, the system or computer readable media shown in FIG. 6 implements the method, but other systems may be used. An image processor performs the various detection, determination, placement, refining, and calculating acts. An ultrasound scanner performs the scanning and output acts. Other devices may perform any of the acts, such as network interface or display device performing the output act.

The acts 32-40 are performed without further user input. The user may activate the process, such as configuring an ultrasound system for valve detection and activating the process. The user may shift the transducer until images show the cardiac region likely to include the valve or a confidence value above a desired level. The user does not indicate a location of the valve or cardiac flow sample region or plane in the cardiac flow region on the images. The processor automatically identifies the valve, valve anatomy, and/or cardiac flow measurement area without user input other than activation and scanning position. In alternative embodiments, a semi-automatic process is used where the user confirms or guides the process by indicating one or more locations and/or indicating changes due to proposed treatment.

The method is implemented in the order shown or a different order. For example, acts 32 and 34 may be performed simultaneously as the detection provides the confidence.

Additional, different, or fewer acts may be performed. For example, one or more of acts 30, 34, and 38 are not provided, such as where the ultrasound data is loaded from memory (act 30), confidence is not used (act 34), and/or refinement is not used (act 38). Acts for configuring, initiating, or use of output information may be provided.

The acts are performed in real-time, such as during ultrasound scanning of act 30. The user may view images of act 42 while scanning in act 30 to acquire another dataset representing the cardiac volume. Measurements and/or images of automatically detected anatomy may be provided in seconds, such as ten or fewer seconds. The flow is quantified during the scanning, within 1-2 seconds of scanning for a given volume, and/or is updated in an on-going basis (e.g., with less than 0.5 second intervals). Alternatively, the acts are performed as desired by a surgeon regardless of whether a patient is currently at the facility or being scanned. The acts may be performed during an appointment or off-line in a review period. The images may be associated with previous performance of one or more of the acts in the same imaging session.

In act 30, a cardiac region of a patient is scanned with ultrasound. An ultrasound transducer, such as an array of 32, 64, 128, 256 or other number of elements, is positioned against the patient. For transthoracic echocardiography (TTE), the transducer is positioned on the chest of the patient such that the acoustic energy passes between ribs of the patient to scan the heart or portion of the heart. For transesophageal echocardiography (TEE), the transducer is positioned in an esophagus of the patient such that the acoustic energy scans the heart. For intracardiac catheter echocardiography (ICE), the transducer is in a catheter positioned within the cardiac system (e.g., scan from within the heart). A handheld or machine positioned probe is used on the skin surface, the cardiac system, and/or in the esophagus of the patient. Other types of ultrasound imaging may be used.

Any format for scanning may be used, such as linear, sector, Vector®, or other format. The distribution of scan lines is in three-dimensions to scan a volume of the cardiac region. The volume is scanned using electronic and/or mechanical steering (e.g., wobbler array). The transducer is held in place or moved to scan the volume.

The scanning transmits acoustic energy. In response to the transmissions, acoustic echoes are received. Different structures or types of structures react to the acoustic energy differently. Using beamforming, the cardiac region is sampled. For rapid volume scanning (e.g., repeat the scan every 0.5 seconds or faster), plane wave or broad transmit beams are formed. Multiple, such as 4, 8, 16, 32, 64, or other number, of receive beams are formed in response to each transmit beam or wave front. In alternative or additional embodiments, cardiac or ECG gating is used to scan in synchronization with the cardiac cycle. Transmissions and receptions from different cycles but at the same time relative to the cycle may be combined to sample the cardiac region. For dynamic assessment, the patient is repetitively scanned throughout the heart cycle and/or at different phases in different heart cycles.

For patient specific modeling, sets of data are obtained by scanning. The sets represent the cardiac region at different periods or phases of the cardiac cycle. Sets of data representing the volume multiple times during a heart cycle are acquired by scanning. The ultrasound data corresponds to a data set interpolated to a regular 3D grid, displayed images (e.g., detected and scan converted ultrasound data), beamformed data, detected data, and/or scan converted data. Imaging data may refer to ultrasound scan data used for imaging, but not necessarily of a displayed image. The ultrasound data represents the volume or 3D cardiac region of the patient. The region includes tissue, fluid or other structures.

The tissue response to the acoustic energy is detected. The receive beamformed samples are processed to represent the intensity of the echoes from the location. B-mode detection is performed. The B-mode data represents the tissue in the cardiac region. Using thresholding and/or filtering, signals associated with fluid are removed. Since the intensity of return from fluid is relatively small, B-mode data may include little or no signal from fluid. The distribution of B-mode data shows the shape of a structure or spatial aspect (i.e., morphology). The B-mode data is of the echoes at a fundamental (transmit) frequency or a harmonic thereof (e.g., second harmonic). In alternative embodiments, Doppler tissue imaging or other mode is used to detect the tissue response.

The fluid response to the acoustic energy is estimated. Flow data representing the fluid in the cardiac region is estimated. Since fluid is typically moving, the change associated with the movement may be used to represent the flow. Doppler processing, whether relying on the Doppler phenomena or based on other ultrasound processing, estimates the flow data. A shift in frequency may be used to estimate the energy, velocity, variance, or combinations thereof of the flow of fluid. For example, the Doppler velocity is estimated as a velocity value or the shift frequency. Other flow estimation may be used, such as determining motion between samples from different times using correlation. Any flow or color-mode estimation may be used, such as color Doppler flow.

In alternative embodiments, the B-mode or tissue response data and the flow mode or fluid response data are acquired from a memory. Previously acquired information is loaded or received for further processing to detect the valve.

In act 32, an image processor detects one or more valves. The valves are detected by fitting valve modes to the ultrasound data, such as the B-mode data. In one embodiment, valve models are fit by using multi-channel image features from both B-Mode and color Doppler, knowing that anatomy (i.e. tissue) cannot spatially coincide with a color Doppler signal (i.e. blood pool). The detection finds one or more landmarks or anatomical components. For example, the anatomical landmarks are, but not limited to, aortic annulus and LVOT, or mitral valve annulus and free edge. Aortic root, aortic leaflets, other aortic landmarks, mitral valve leaflets, and/or other mitral valve landmarks may be used.

Any valve is detected, such as the aortic, mitral, pulmonary, or tricuspid valves. The detection is of the overall valve anatomy or of specific anatomy of the valve, such as the annulus, leaflets, root, free edge, outflow tract, or other landmarks. Two or more valves may be detected, such as separately detecting the aortic and mitral valves. A combined model using two or more valves may alternatively be used. Valve models may be obtained from two different acquisitions, each optimized for inflow and outflow, in order to quantify flows that are rather parallel to the beam direction. The results may be combined.

The valve or valve anatomy are detected for each frame of volume data or time (i.e., phase of the cardiac cycle). By repeating the detection, the valve or valve anatomy is found through a sequence of frames or over time, such as over one or more heart cycles. Alternatively, the valve is detected at one time and then tracking is used to model the valve at other times based on the detection at that one time. Any tracking may be used, such as a relying on optical flow with a motion prior and boundary detection.

B-mode data is used to detect. Alternatively, both B-mode and flow data are used to detect the valves. While the valve is a tissue structure, flow around the valve may be distinctive or indicate the location of the valve. A machine-learnt classifier uses input features from both the B-mode and flow-mode data of the patient to detect the representations of the valve of the patient. In one embodiment, the valve or anatomy is detected over time using multi-channel image features from both B-Mode and color Doppler. The detection may search only a sub-set of locations or voxels since anatomy (i.e., tissue) cannot spatially coincide with the color Doppler signal (i.e., blood pool). The detection is applied to just the tissue locations and not the flow locations. The detection is constrained to locations without flow-mode data.

The valve anatomy is detected directly. The classifier is applied to the data to locate the valve anatomy. The location or locations with the greatest probability are selected. In other embodiments, a bounding box is first detected. While the bounding box does not exist as anatomy, the classifier may be trained to locate a rectangular prism or other shape surrounding the likely locations of the valve anatomy. The more computationally expensive classifier for detecting the valve anatomy is then applied just within the detected boundary box.

To detect the valve and/or boundary box, tissue and/or fluid features are calculated. The features are not specific cardiac, valve anatomy or jet features, but are features for input to a classifier. Anatomy or jet features may be used as input features for the classifier. Other features, such as the B-mode data and flow data or values derived there from, may be used. For classification, input features from the B-mode data and/or the flow data are input. A set of B-mode features is input, and/or a set of flow data features are input. In alternative or additional embodiments, a given input feature is a function (e.g., sum) of both types of data. In other embodiments, only B-mode or only flow mode data is used. Additional features, such as features not from scanning or images, may be used as well.

To extract both morphological and functional information, 3D features are computed for these multiple channels. 2D, 1D, or point features may be used.

Any type of input features may be calculated. For example, gradients of the data, the data itself, detected anatomical or jet features of the data, maximum, minimum, other statistical, or other information are calculated from the B-mode and flow data. In one embodiment, 3D Haar wavelets and steerable features are used. These features are relatively fast to compute and capture information well. In other embodiments, deep learning is used to train. The deep learning learns filter kernels to be applied to the ultrasound data for classification.

In one embodiment, the global valve anatomy is localized. A position, orientation, and/or scale of the valve region or bounding box within the cardiac or scan region is located. The global valve anatomy is the entire valve or a portion of the valve without being a specific part and/or with being a collection of multiple parts. The valve as distinguished from heart wall, other valves, or other heart anatomy is located.

A bounding box, sphere, segmented surface, or other shape is used to designate the global valve anatomy. In one embodiment, the global location of the valve anatomy is represented by a bounding box parameterized with an affine transformation. The bounding box $\theta$ is parameterized for translation T (position), rotation R (a), and scale S along the three dimensions of the volume. Other parameterizations may be used, such as with just translation and rotation (not scale) or with one or more aspects limited to fewer than three dimensions.

In this representation, the position of the bounding box is given by the barycenter of the valve. Other indications of position, such as a corner of the box, may be used. The scale is chosen to enclose the entire underlying valve anatomy. The shape or scale may include other information, such as including tissue from adjacent structures of the heart and/or part or all the regurgitant jet. The orientation is defined by the trigonal plane. Other references for scale and/or orientation may be used.

The global valve anatomy, such as represented by the bounding box, is located using some or all the input features. Different features may be used for different classifiers. The tissue ultrasound features derived from B-mode data and the flow ultrasound features derived from Doppler data (e.g., derived from velocity) are used to locate the valve. Some features may be more determinative of location, rotation, and/or scale than others. Some features may not be used for global localization. Since the view angle and other scan parameters may vary from scan to scan, all the calculated input features may be used.

The global position of the valve is located by a classifier. The feature values are input to the classifier, and the classifier outputs the bounding box, parameter values, or other indicator of the global position of the valve. The classifier is a machine-learnt classifier. Based on the extracted input features, a discriminative classifier or classifiers are trained to detect the location of the valve. Different machine-learnt classifiers detect different valves. Alternatively, one machine-learnt classifier detects multiple valves.

Other discriminative classifiers may be used for other detections, such as for locating the valve more explicitly, for detecting parts of the valve, or for detecting the regurgitant orifice. To achieve robust and accurate detection results, the search is performed in a hierarchical manner. The global location of the valve anatomy uses one classifier, followed by the estimation of valve anatomy, and then following by the regurgitant orifice and/or part specific detection. The same or different types of classifiers may be used. Since the classifiers are used for different purposes, the resulting machine-learnt classifier for one stage is different than for another stage even if using a same type. Fewer stages may be used, such as detecting a bounding box and then detecting the valve without a stage for the regurgitant orifice.

Any machine learning method may be used for one or more stages. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron) as well as deep neural networks or deep image-to-image networks, mixture models, or others. A probabilistic boosting tree may be used. Error-correcting output code (ECOC) may be used.

The classifier is trained from a training data set using a computer. Any number of expert annotated sets of data is used. For example, tens or hundreds of volume sequences representing the heart and including the valves are annotated. The annotation indicates valve landmarks, global locations, surfaces, or other relevant information within the volumes. The anatomies of each volume are annotated. This large number of annotations allows use of a probabilistic boosting tree or other machine learning methods to learn relevant features over a large pool of 3-D Haar, steerable features, and/or other features as well as image intensities directly in the case of neural networks. Each classifier uses the data sets and annotations specific to the anatomy or box being classified.

In one embodiment, the classifier is a knowledge-based probabilistic model, such as marginal space learning using a hierarchical search. A database of known cases is collected for machine learning, providing a database-driven knowledge-based approach. For training data, three-dimensional context information is preserved and guides the detection process. Knowledge is embedded in large annotated data repositories where expert clinicians manually indicate the anatomies and/or measurement indicators for the anatomies. The detectors are trained on a large number of annotated 3D volumes. The classifier learns various feature vectors for distinguishing between a desired anatomy and information not being detected. In alternative embodiments, the classifier is manually programmed.

For learning-based approaches, the classifier is taught to distinguish based on features. For example, the probability model algorithm selectively combines features into a strong committee of weak learners based on Haar-like local rectangle filters whose rapid computation is enabled using an integral image. Features that are relevant to the anatomies are extracted and learned in a machine algorithm based on the experts' annotations, resulting in a probabilistic model. A large pool of features may be extracted. The training determines the most determinative features for a given classification and discards non-determinative features. Different combinations of features may be used for detecting different anatomies, the same anatomy at different times, and/or the same anatomy associated with different translation, rotation, or scale. For example, different sequential classification stages utilize different features computed from the 3D volume data. Each classifier selects a set of discriminative features that are used to distinguish the positive target from negatives. The features are selected from a large pool of features.

A tree structure may be learned and may offer efficiency in both training and application. Often, amid boosting a multi-class classifier, one class (or several classes) has been completely separated from the remaining ones and further boosting yields no additional improvement in terms of the classification accuracy. For efficient training, a tree structure is trained. To take advantage of this fact, a tree structure is trained by focusing on the remaining classes to improve learning efficiency. Posterior probabilities or known distributions may be computed, such as by correlating anterior probabilities together.

To handle the background classes with many examples, a cascade training procedure may be used. A cascade of boosted binary-class strong classifiers may result. The cascade of classifiers provides a unified algorithm able to detect and classify multiple objects while rejecting the background classes. The cascade structure corresponds to a degenerate decision tree. Such a scenario presents an unbalanced nature of data samples. The background class has voluminous samples because all data points not belonging to the object classes belong to the background class. Alternatively, the classifiers are sequentially trained without cascade.

The probabilistic boosting tree (PBT) unifies classification, recognition, and clustering into one treatment. A probabilistic boosting tree is learned for each anatomy or stage of interest. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques. Other probabilistic machine training result in detectors that provide confidence values.

In one embodiment of the classifier for global valve localization, a marginal space learnt classifier is applied. The global region is located in stages or with sequentially determined translation, rotation, and scale along three-dimensions. The position within the volume is first classified, and then the rotation at that position is classified, followed by the scale given the position and rotation. The machine-learned matrix finds position candidates around the valve based on Haar and steerable features. The position candidates are then successively refined by rotation and scaling candidates. This defines a region of interest for the valve, such as the bounding box.

The bounding box or valve region detection is used to specifically detect the valve or valve anatomy. Further classification by another machine-trained classifier is used to detect the location, orientation, and/or scale of the valve or valve anatomy as represented by the ultrasound data. The bounding box or region detection is used to limit the search for the valve anatomy. Alternatively, the first stage of classification is to detect the valve anatomy without first detecting the bounding box.

The valve is detected by detecting the whole structure and/or by detecting specific landmarks or parts of the valve. The anatomy of the valve is identified in the data. For example, the annulus and/or closure line are identified. In other examples, other anatomies, such as leaflets and/or chordae, are identified. Any part of the valve may be located. Given the identified valve region, anatomical structures of interest, such as the annulus and the closure line, are detected.

Any representation may be used for identification. For example, the annulus, leaflets, free edges, root, and closure line are represented as fit curves or detected surfaces. Anatomical landmarks may be represented as volume shapes, areas, surfaces, lines, curves, or points.

One or more machine-learnt classifiers are used to identify the anatomic structure or structures. Any of the classifiers discussed above, but trained for locating specific or groups of specific anatomic structure of the valve may be used. The classifier locates the entire structure. Alternatively, different points are sequentially classified. The global valve region is searched point by point. For each point, input features for the point and surrounding points are used to classify the probability that the point is part of the anatomy.

The features are applied to a matrix representing a machine-learnt classifier. In one embodiment, the classifier is a PBT classifier, so provides the target posterior probability. The points with the highest probability, probability over a threshold, or other criteria are selected as representing the anatomy. Points with lesser probabilities are not selected. The classifier outputs the probabilities for each point tested, and the points with the greater or sufficient probability are used as indicating the anatomy.

The detected anatomy may be used as the output. The variance may be great due to the resolution of the data. There may be little direct correlation of the highlighted or detected lines to the B-mode structure shown. Since the valve moves rapidly and is relatively small as compared to the resolution of ultrasound, a patient-specific valve model may be fit to the detected anatomy. A patient-specific valve model is fit to the input data to visualize the valve anatomy and to assist therapy planning and procedure simulation. A model is fit to the detected anatomy of the specific patient, so that the fitting causes the model to be patient-specific. For example, the annulus, leaflets, free edge, root, or other landmarks of the model are fit to the corresponding detected anatomy. In the case of the left heart, valve models may include (1) the aortic annulus, aortic root, leaflets, other landmarks, and/or left ventricle outflow tract or (2) the mitral valve annulus, leaflets, other landmarks, and free edge. Any combination of different anatomy of the valve may be modeled. The fitting results in adjustment (e.g., translation, orientation, and/or scaling) of other anatomy represented in the model to the patient.

Any model of the valve may be used, such as a mathematical or programmed model. In one embodiment, a statistical shape model is used. A statistical shape model of the valve is built from a training set. Any number of samples may be used to determine the position and/or deviation probabilities for the valve anatomy. A mesh, feature collection, sample grid or other distribution is used to represent the model.

The model is labeled. The anatomy is indicated by the model, such as indicating a position of the posterior leaflet, the anterior leaflet, the annulus, and the closure line. The model provides detailed information missing from, not easily viewable, or also included in the data representing the patient. For example, the closure line and annulus are not easily viewable in B-mode images. The model clearly indicates the locations for the closure line and annulus. For cardiac flow calculation, the model label includes a position of one or more cardiac flow sampling regions relative to the detected valve. In alternative embodiments, no labeling is provided.

The model is transformed to become a patient-specific model. The model is altered or fit to patient-specific data. For example, a statistical shape model is transformed using the detected anatomy. The anatomy of the statistical shape model is transformed to fit with detected anatomy. The spatial distribution probabilities of the statistical model may limit the transform so that the anatomy more likely represents the norm or possible arrangements. Given the previously detected anatomy, a patient-specific valve model is constructed to visualize the anatomical structure.

Any fitting may be used. For example, thin-plate-spline (TPS), Gaussian bending, non-linear ICP, or other non-rigid transforms are applied. In one embodiment, a number (e.g., 13) of points identified of detected anatomy are selected from both the statistical shape model and the patient anatomy. Rather than using points identified as part of the detection, the detected anatomy may be resampled for the transformation. The selected points are equally spaced along the detected anatomy. These anchor points are used to compute the TPS transformation, which deforms the valve model (e.g., statistical shape model) non-linearly to fit the detected anatomy. Only some or all the anatomy of the model are transformed. The fit statistical shape or other model provides the location of the labeled anatomy, surface, or other valve information specific to the patient.

Figure 2:
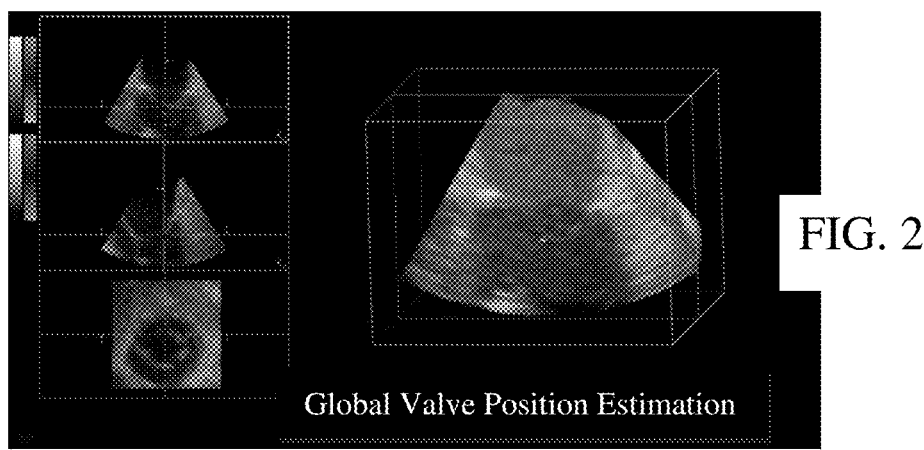
FIG. 2 is an example ultrasound image display (i.e., 3D rendering and multi-planar reconstructions) showing the mitral valve.
Figure 3:
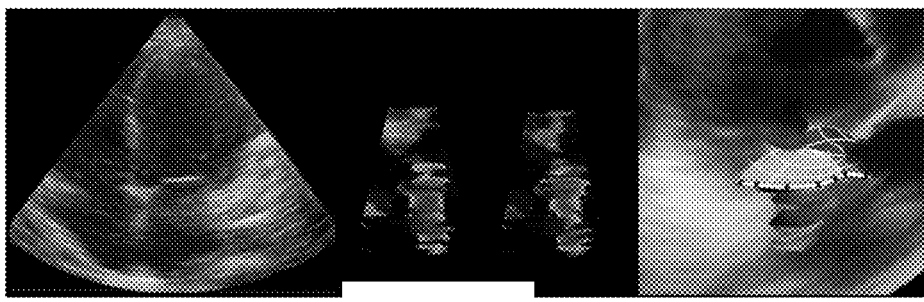
FIG. 3 shows example B-mode and flow mode images and an example fitted model image of the mitral valve.

FIG. 2 shows a volume rendering and multi-planar reconstruction images of valve region. The image processor detects the valve. As shown in FIG. 3, a fit model in the form of a mesh captures the valve anatomy. The left and center images of FIG. 3 show B-mode and Doppler velocity images. The valve may be shown in the images, but is not very distinct or is difficult to locate. To assist the sonographer, the valve or valve anatomy may be detected and highlighted, such as shown in the right image of FIG. 3.

By fitting the model or other detecting at different times through a sequence of data or volumes, the dynamic behavior of the valve is captured. The model may incorporate physics or other dynamic behavior to limit change over time. In other embodiments, the valve is detected with the bounding box and/or specific landmarks without fitting a model.

In act 34 of FIG. 1, the image processor determines a confidence for the detecting of one or more of the heart valves. The confidence indicates a likelihood that the detection is accurate and/or complete. For example, the confidence reflects whether the entire valve, part of the valve, or none of the valve is represented in the ultrasound data and/or a noise level or artifacts resulting in less assurance that the valve has been accurately detected. In some cases, one of the valves is not fully covered by the field of view or not even present in the ultrasound data. For TEE imaging, the field of view may not entirely cover the aortic valve. This situation may be detected by a low confidence score of the position detector of the aortic valve.

The confidence is output by the detection. A level of detection indicates the confidence. Where a probabilistic detector (e.g., machine-learnt classifier using probabilities) is used, the detector both indicates the bounding box (e.g., global location), the valve, and/or landmarks and indicates a confidence. The confidence is for the most likely detection. Where multiple possible locations are detected, the one with the highest confidence is selected. This highest confidence is the confidence score to be used.

One confidence for two or more valves may be provided. For example, confidences from separate detections are averaged or a least confidence from the different detections is selected. Alternatively, separate confidence scores are used for the different valves. In other embodiments, the detection is of a plurality of valves using one classifier, so one confidence score is used.

Figure 4:
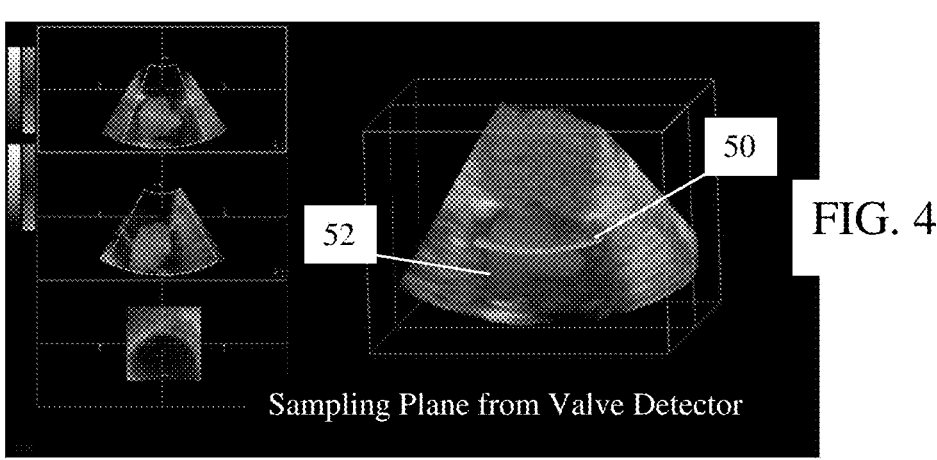
FIG. 4 is an example ultrasound image display with a placed sample plane.

In act 36, the image processor places a measurement region for cardiac flow. Any measurement region may be used, such as a volume, area, line, or point region. In one embodiment, the measurement region is an area of a plane in either Cartesian or polar/spherical coordinate format. The area may be a planar area or a curved surface. The planes are measurement planes or planes used to define regions of interest for further processing. The sampling plane may be defined on a Gaussian sphere passing through anatomy (e.g., the mitral annulus or LVOT) since a sampling plane in the acoustic space (e.g., polar or spherical coordinate system) with a constant distance to the transducer corresponds to a Gaussian sphere in the Cartesian space, centering the transducer at the tip of the pyramid. FIG. 4 shows the sampling plane 50 as a disc or curved area placed relative to a detected valve.

The valve detector or detectors initialize the cardiac flow measurement region or regions, such as an area or areas. Rather than initializing by the user or manually, information obtained from the valve detectors is used. The initialization is of a position, orientation, shape, and/or scale of the measurement region. Alternatively, the initialization is of a center point or seed point used to then locate a remainder of the area or region using image processing.

Any aspect of the valve detection may be used. Sampling planes, measurement area, or other cardiac flow region may be initialized by using the bounding box, valve anatomy (annulus, leaflets, root), and/or valve landmarks. For example, a center of the bounding box of a valve model is used. As another example, the aortic root, leaflets, and/or left ventricle outflow track curvature (e.g., tangent to the lowest left ventricle outflow track curve) are used for a measurement area placement in the left ventricle outflow track. In yet another example, the mitral valve leaflets and annulus are used for a measurement area placement for mitral flow.

Where a model is fit, the model may include a label or annotation defining the measurement region relative to the detected valve. Where a bounding box or landmarks are detected, the measurement region may have a set, default or predefined spatial relationship with the box and/or one or more landmarks. The measurement region is located (e.g., position, orientation, and/or scale) based on the valve detection. The spatial relationship from the detected valve information to the placement is learned with machine learning or programmed based on expert knowledge.

The placement positions the measurement region at a valve, such as at the mitral annulus. Alternatively, the placement positions the measurement region spaced from the valve. The valve detection is used for placement away from the valve. For example, a sample plane or measurement area is placed slightly below a valve, such as 3-10 mm from the valve. In another example, for the mitral valve, the inflow plane is placed in between the mitral valve annulus and the mitral valve free edge rather than at the mitral valve annulus. In yet another example, an outflow plane is placed below the aortic valve annulus, at the end of the left ventricle outflow tract. Rather than placement in the heart, the placement based on the detected valve may be in a vascular structure (e.g., across a stenosis).

The detection of two or more valves may be used to place one or more measurement regions. For example, the measurement surface area is placed in the cardiac flow region spaced from the two or more valves. In placing the measurement surface area at the left ventricle outflow tract, spatial information from detection of both the mitral and aortic valves may be used. The orientation and size avoid the mitral valve and an anterior leaflet while the area is centered based on information from the aortic valve. Information from different valves may be used to determine different aspects of the placement (e.g., position, orientation, scale, and/or shape). Information from different values may be used to determine a same aspect of the placement, such as the relative position of the valves indicating a position of the measurement area. The flow plane may be initialized differently based on the geometrical elements of the valve models.

The measurement surfaces are oriented. For example, the surfaces have an orientation set relative to the detected valves. The spatial extent or scale of the surface is predetermined or based on detected anatomy. For example, the spatial extent is set to the aortic/mitral valve annulus diameters, respectively. The orientation and/or the size of the sampling plane may be adjusted based on the orientation and/or size of the bounding box, the relative positions of landmarks, and/or another valve information. The automatically determined sampling locations may be modified by a user.

Other information may be used for placement. For example, flow (e.g., Doppler velocity, energy and/or variance) information is used in placing the measurement region. The position based on flow and position based on anatomy may be averaged. Alternatively, the position based on anatomy (e.g., detected valve or valves) is adjusted or refined (see act 38) based on the flow.

In one embodiment, the confidence is used in addition to the detected valve information. The confidence indicates the likelihood of accurate valve detection. A confidence below a threshold level may mean the valve or valve associated landmark is inaccurately detected. As a result, the position of the measurement region is based off other information, such as a valve detected with greater confidence. For example, the outflow plane for measurement is placed using a mitral valve model instead of the aortic valve model where the confidence for the aortic valve is below a threshold. Confidence may be used to trigger other detection. A low confidence for one valve may trigger detection of non-valve anatomy. For example, the outflow plane is placed using a combination of the mitral valve model and a triggered left ventricle outflow tract detector. A plurality of different placements may be provided where the one to use is based on the level or degree of confidence. Combinations of confidence from detection of different valves may be used to select the placement.

The anatomy and/or planes are tracked over time. Tracking may ensure temporal consistency and smooth motion and may avoid drifting and outliers. The left ventricle boundary, mitral annulus, aortic valve, and/or left ventricle outflow tract are tracked over time. Alternatively, the detection is repeated for frames of data representing the cardiac region at one or more other phases.

In one embodiment, the measurement planes and/or surfaces are tracked with a machine-learned detector. For example, a Bayesian network of local features and the plane position from another frame are used for tracking. The tracking is performed for each frame $t = 1, \ldots, T-1$ where T is total number of frames. The data used for extracting features is the B-mode data, velocity data, or combinations thereof. The inputs for a given frame also include the left ventricle and measurement plane locations, $X_{t-1}$, from the previous frame $t-1$.

In the subsequent frames, the measurement planes are tracked using the Bayesian approach. The Bayesian function is represented as:

$$\text{argmax of } X_t p(X_t \mid Y_{1:t}) = \text{argmax of } X_t p(Y_t \mid X_t) p(X_t \mid Y_{1:t-1})$$

where $Y_{1:t} = (Y_1, \ldots, Y_t)$ are the local features and image templates from the first t frames $I_{1:t} = (I_1, \ldots, I_t)$. The image template is the prior plane and/or anatomy locations. $X_t$ is used to denote a concatenation of the mesh point positions, $X_t = [X_1, \ldots, X_n]$, which are estimated at the current time instance t, and n is the total number of points in the model. This Bayesian function is solved using any optimization technique.

Starting from the detection result at the initial frame, the model deformations are propagated to neighboring frames using both the learned features and the local image templates. The tracking indicates the location of the planes at different times. Other tracking may be used, such as optical flow, boundary detection, and/or motion prior information. For example, the sampling planes representing the mitral inflow tract and the left ventricle outflow tract are tracked by fusing information from multiple cues, including optical flow, boundary detection, and motion prior.

Figure 5:
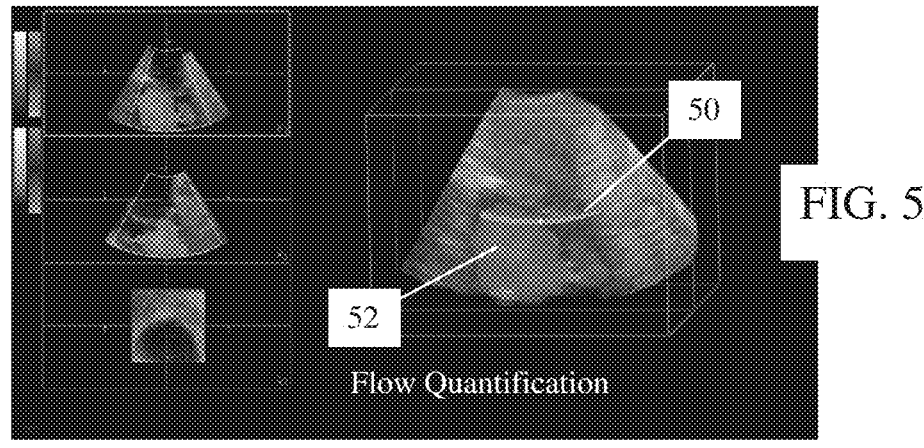
FIG. 5 is an example ultrasound image display for flow quantification with a placed sample plane at a different time than for FIG. 4.

FIG. 4 shows a flow region 52 at one time in a 3D rendering. FIG. 5 shows the flow region 52 at a different time or phase in a 3D rendering. The sampling plane 50 is placed in the cardiac flow region 52 and is also in a different spatial location based on the tracking. Whether by separate detection for each phase or initial detection in one phase and tracking in the other, the detected heart valve or valves are used to determine the placement at different times.

In act 38 of FIG. 1, the placement of the measurement region (e.g., area surface) for any given or each phase is refined. The refinement may be based on other anatomy information and/or flow information. In one embodiment, the refinement of the placement is based on aliased flow, relative flow, maximum flow, and/or a smoothness of out-flow and/or inflow as a function of time. For example, the locations of inflow and outflow planes are refined and optimized by exhaustive search around the initial placement location to ensure robust flow quantification. The search includes variation in position, orientation, scale, and/or shape in any search pattern. The placement is fit to the ultrasound data using any criteria. Example optimization criteria include avoiding aliased flow, avoiding excessive values (i.e., likely noise values), presence of measured flow, and/or smoothness of the resulting outflow and/or inflow over time. Placement with greater smoothness, minimized undesirable flow, and/or maximized desirable flow is use identified in refinement. A machine learning based classifier or regressor may be used as optimization criterion (e.g., using a convolutional neural network, deep image-to-image network, marginal space deep learning or other learning based classification or regression methods).

In one embodiment, the orientation of one or more surfaces is refined. The position, scale, or other information may be refined as well or instead. The refinement relies on velocity values, but may alternatively or additionally use other data such as B-Mode data and/or models generated thereof (e.g., models of the left or right ventricle), to minimize impact of possible flow artifacts (e.g., where flow artifacts coincide with actual tissue).

To refine the orientation as a function of the velocity values, a two- or three-dimensional distribution of flow at the anatomy of interest is used. Principal component analysis (PCA) may be used to determine the center, orientation, and size of the flow. The disk is moved to the centroid of the non-zero voxels of the flow volume and re-oriented to match the principal axes of flow. The disk may be re-sized based on PCA variation along an axis. The mitral annulus and left ventricle outflow tract have jets or flow regions. The flow at the same time as the reference frame or from another time is used. For example, a cross section through both regions is extracted. The same cross-section, flat plane extends through both regions. The surfaces are reoriented based on the direction of flow from the segmented flow region of the cross-section. The planes are reoriented so that the plane is orthogonal or is more orthogonal to the direction of the jet or flow. The reorientation may be limited, such as providing a range of divergence from orthogonal to the transducer.

The tracking is refined in one embodiment. For example, a mean shift algorithm is used for local refinement. Based on the mitral annulus and left ventricle outflow tract locations obtained from the tracking, a local refinement places the measurement planes accurately using the mean shift approach. The plane is shifted to provide the maximum flow. The shift is by translation and/or rotation. As a result, the areas associated with volume flows are computed consistently based on the anatomical structure of the left ventricle. In another realization, temporal consistency is obtained by optimizing refined disk location, orientation and size to fit over time since there may be different results when optimized for each frame independently. This could be done by a Markov based approach (e.g., belief propagation, Viterbi or other graph based algorithms), in combination with random sample consensus (RANSAC) to remove temporal outliers.

Other processes may be included. For example, any aliasing in velocity values is removed. Any unaliasing may be used. The velocities may be aliased. In color flow images, aliasing is a common issue which describes exceeding of the color Doppler Nyquist velocity, causing ambiguity for velocities beyond the Nyquist level. Due to the setting of the pulse repetition interval, higher velocities may wrap around as different values. To avoid inaccuracies associated with aliasing, the velocities are unaliased.

In one embodiment, the velocity values are further corrected for the scan angle prior to calculation. Ultrasound scanning measures the velocity along a scan line, so is the velocity to or from the transducer. When the flow is in a different direction, the estimated velocity value may be lower than the actual velocity of the flow. Where the transducer is oriented to scan along a line orthogonal to the area of flow being measured, the velocities reflect flow along the desired vector. Where the acoustic window results in another angle, the velocities may be corrected or used to determine the flow along the desired direction. A direction of flow is determined, such as from user input, boundary analysis, the valve model, or other source. The velocity is corrected based on the angle of difference between the scan line and the direction of flow.

In act 40, the image processor calculates a cardiac flow value from flow data of the volumetric ultrasound scan for the measurement region. Example cardiac flow values include inflow, outflow, regurgitant flow, and/or stroke volume. Any parameterization of the flow may be used, such as a volume flow. The volume of blood that passes through this location during a cardiac cycle may be calculated. Measurements indicating cardiac performance (e.g., cardiac output) and pathologies (e.g., regurgitant volume) may be derived from the volume of blood. The measurement region, such as a surface area, is used for the calculation. For example, the average, maximum, variance over time or space, or sum of velocity of flow at the measurement surface area is calculated.

The calculation may be repeated over time. For example, the tracked locations of the measurement regions at the mitral annulus and left ventricle outflow tract are used to construct and adjust the sampling planes of the color flow data. The flow volume is computed by aggregating the sampled color flow values in the space defined by the measurement region. To compute the integral volume of the mitral inflow and left ventricle outflow tract outflow, the circular or other shaped area enclosed by the mitral annulus and LVOT ring is used.

In one embodiment, the volume flow is calculated. The volume flow is a measure of the fluid volume passing through the measurement surface area over a period. For example, the area of the mitral annulus is multiplied by the velocity average of the area, summed over each time increment for a desired period. As another example, the volume flow, $Vf_t$ is computed from the corrected velocity data as:

$$Vf_t = \Sigma v'_i * dA_i^{(t)}$$

where v' is the estimated velocity after de-aliasing and $dA_i^{(t)}$ is the unit area of each sampling point. To compute the volume of the mitral inflow and the left ventricle outflow tract outflow, the areas enclosed by the mitral annulus and the left ventricle outflow tract ring are used based on sample points in the measurement region with sufficient velocity or flow.

Other measures of the volume passing through an area as a function of time may be used. For example, instantaneous volume flow (i.e., volume of flow at a phase or time) is calculated. The volume flow for the mitral annulus and the left ventricle outflow tract should be the same or similar, so the two values may be averaged. Alternatively, the two values are calculated separately. Curves of the volume flow as a function of time may be calculated. Separate cardiac flow values may be calculated for separate measurement regions.

The calculation may be limited to avoid flow during a portion of a heart cycle. For example, regurgitant flow is avoided in inflow, stroke volume, or outflow calculations as these measurements quantify the cardiac performance and physiology rather than the pathology directly (regurgitation). Regurgitation may be quantified from accurate inflow and outflow measurements. Regurgitant flow occurs during particular phases—during diastole for aortic and pulmonary valve and in systole for mitral and tricuspid valve—for particular cardiac flow regions across the valve. Regurgitation is very high velocity flow, which is difficult to accurately quantify directly using any Doppler imaging method (other than continuous wave). By avoiding calculating the inflow or outflow during regurgitant flow, a more accurate measure of inflow and outflow may be provided.

Any timing source may be used. For example, ECG signals are used. When the ultrasound acquisition is not gated, the ECG may not accurately match the actual image contents (e.g., there may be a small temporal lag). As another example, the timing is based on the valve detection, therefore based on the B-mode image information directly. The model of the valve over time includes labels indicating times of flow of interest. While a valve is closed, the corresponding flow (e.g., outflow or inflow) is not calculated. The timing from the tracked and/or detected valves is used to limit the calculation. ECG may be used to decrease the runtime of valve tracking and only track around the ED and ES frames in the vicinity of which valves open and close. In another realization, a combination of flow, valve models and ECG may be used to determine an accurate timing, for instance, to address special cases such as stenotic valves, which only open to a minor extent.

In act 42, the image processor, ultrasound scanner, network interface, memory interface, and/or display device output an image of the cardiac flow value. For example, the quantity or quantities are displayed on a display. The quantity may be displayed as an alphanumerical value. Alternatively or additionally, the quantity or calculated cardiac flow value is displayed in a graph. For example, a graph of volume flow over time is generated. The volume flow between pairs of frames or volumes is calculated and graphed to show volume flow over time. As another example, an image of anatomy and/or flow is highlighted based on the cardiac flow value, such as tinting the cardiac flow region represented in an image based on the level of the calculated value.

The quantity may be displayed with a two or three-dimensional image. For example, the B-mode, velocity, other data, and/or combinations thereof is rendered using three-dimensional rendering. A multiplanar reconstruction may be generated from the data. An image of the measuring surface may be generated (see FIGS. 4 and 5). An image of the model or detected anatomy (e.g., of the mesh for the valve or meshes for valves) may be generated (see FIG. 3). The quantity or quantities may be displayed with any imaging of the anatomy and/or flow.

One or more two- and/or three-dimensional images may be generated and displayed at a same time. A sequence of images may be generated to show the anatomy over time. Similarly, the cardiac flow value or values are displayed at a same time and/or over time.

Where the image uses velocity values, the corrected velocities are used. As a result, little or no aliasing is shown. The image values are directly or indirectly mapped from the unaliased velocity data. For example, color values correspond to the amplitude of the velocity values. In another example, the image values correspond to a combination of different data, such as phase velocity values and B-mode information. As another example, the color values correspond to a magnitude and/or orientation of a velocity vector derived from the velocity values.

Other information may be provided with the calculated value or values. For example, the confidence is displayed. Any representation of the confidence may be used, such as alphanumeric, graphical, or highlighting. The confidence from the initial detection of the valve and/or from other detections is output. The confidence over time may be output. More than one confidence may be output, such as the confidences from detections of different valves.

The indication of confidence may be used by the physician to aid in diagnosis, prognosis, or planning. Low confidence may be used to indicate further testing or repetition of the scanning is appropriate. Different scanning may be used. Higher confidence may indicate that further scanning or repetition is not needed.

Figure 6:
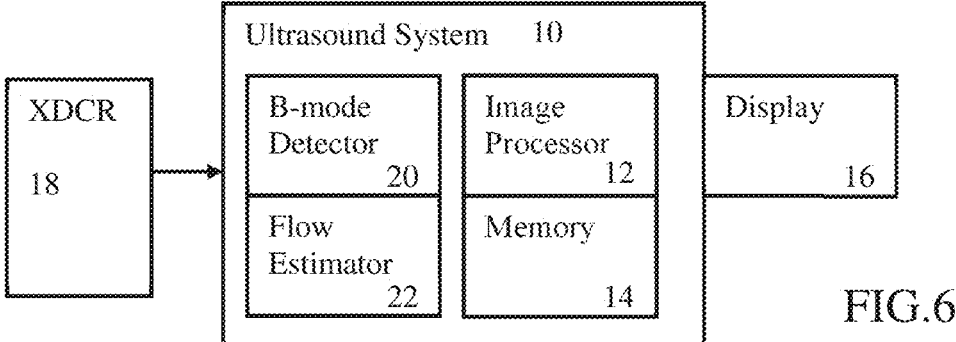
FIG. 6 is a block diagram of one embodiment of a system for detecting cardiac flow.

FIG. 6 shows a system for detecting cardiac flow. The system includes a transducer 18, an ultrasound scanner 10, and a display 16. The ultrasound scanner 10 includes a B-mode detector 20, a flow estimator 22, an image processor 12, and a memory 14. In other embodiments, the system is a workstation, computer, or server for detecting using data acquired by a separate system in real-time or using previously acquired patient-specific data stored in a memory. For example, an ultrasound scanner 10 is provided for acquiring ultrasound data representing a volume, and a separate database, server, workstation, and/or computer is provided for detecting valves, placing measurement regions, and calculation cardiac flow. Additional, different, or fewer components may be used.

The ultrasound scanner 10 includes a transmit beamformer, receive beamformer, B-mode detector 20, flow estimator 22 (e.g., Doppler detector), harmonic response detector, contrast agent detector, scan converter, filter, combinations thereof, or other now known or later developed medical diagnostic ultrasound system components.

The transducer 18 is a piezoelectric or capacitive device operable to convert between acoustic and electrical energy. The transducer 18 is an array of elements, such as a multi-dimensional or two-dimensional array. Alternatively, the transducer 18 is a wobbler for mechanical scanning in one dimension and electrical scanning in another dimension. In another embodiment, the array is a one-dimensional array. Multi-dimensional arrays or a plurality of one-dimensional arrays may be provided. The transducer 18 is a TTE, TEE, or ICE-based transducer.

The ultrasound scanner 10 uses the transducer 18 to scan a heart volume of a patient. Electrical and/or mechanical steering allows transmission and reception along different scan lines in the volume. Any scan pattern may be used. For example, a plurality of different planes through the heart is scanned by rocking an array or volume scanning with a matrix array. In one embodiment, the transmit beam is wide enough for reception along a plurality of scan lines. In another embodiment, a plane, collimated or diverging transmit waveform is provided for reception along a plurality, large number (e.g., 16-64 receive beams), or all scan lines.

The scan provides the medical diagnostic ultrasound data representing the heart or valve volume. The scan may be repeated to provide data for the volume at different times. Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode (e.g., Doppler mode), contrast agent, harmonic, or other ultrasound modes of imaging. For valve detection, both B-mode and flow or Doppler mode data are acquired. For cardiac flow calculation, flow or Doppler mode data is acquired.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10.

The memory 14 stores the ultrasound data, such as ultrasound data representing a cardiac volume. The cardiac volume includes at least one valve and other portions of the heart. Vessels may be represented. The memory 14 stores flow (e.g., velocity, energy or both) and/or B-mode ultrasound data. Alternatively, the medical image data is transferred to the image processor 12 from another device. The medical image ultrasound data is a three-dimensional data set or a sequence of such sets (e.g., over one or more heart cycles). The data represents a three-dimensional region.

For real-time imaging, the ultrasound data bypasses the memory 14, is temporarily stored in the memory 14, or is loaded from the memory 14. Real-time imaging may allow delay of a fraction of a second, or even seconds, between acquisition of data and output of imaging using the data. For example, real-time imaging is provided by generating the images substantially simultaneously with the acquisition of the data by scanning. While scanning to acquire a next or subsequent set of data, an image is generated for a previous set of data. The imaging occurs during the same imaging session or patient appointment used to acquire the data. The amount of delay between acquisition and imaging for real-time operation may vary, such as a greater delay for initially locating valve anatomies with less delay for measurements. In alternative embodiments, the ultrasound data is stored in the memory 14 from a previous imaging session and used for measuring and/or generating a planar reconstruction without concurrent acquisition.

The memory 14 is additionally or alternatively a nontransitory computer readable storage medium with processing instructions. The memory 14 stores data representing instructions executable by the programmed processor 12 for calculating cardiac flow. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 12 is a general processor, digital signal processor, three-dimensional data processor, graphics processing unit, application specific integrated circuit, field programmable gate array, digital circuit, analog circuit, combinations thereof, or other now known or later developed device for processing medical ultrasound image data. The image processor 12 is a single device, a plurality of devices, or a network. For more than one device, parallel or sequential division of processing may be used. Different devices making up the image processor 12 may perform different functions, such as an automated anatomy detector and a separate device for performing measurements associated with the detected anatomy. In one embodiment, the image processor 12 is a control processor or other processor of a medical diagnostic imaging system, such as a medical diagnostic ultrasound imaging system processor. The image processor 12 operates pursuant to stored instructions, hardware, and/or firmware to perform various acts described herein, such as controlling scanning, detecting valves, placing a measurement region, and/or calculating cardiac flow.

In one embodiment, the image processor 12 is configured to implement one or more of the acts of FIG. 1. In other embodiments, the image processor 12 is configured to locate the valve, place a measurement region based on the located valve, and use the measurement region to calculate cardiac flow. The detection of the valve anatomy and/or the fitting of the model are performed over time. Tracking may be used for valve detection and/or placement of the measurement region. The locations of the valve and the placement of the measurement region are performed without user indication of a location. Automatic detection is provided.

In on embodiment, the image processor 12 is configured to fit a model of a heart valve over a heart cycle to B-mode data with a machine-learnt classifier. Models may be fit to multiple valves over any number of heart cycles or portion of a heart cycle.

The image processor 12 is configured to locate one or more cardiac flow regions. The location of any cardiac flow region is based on the detected valve or valves. The location may be based, in part, on a confidence output by the machine-learnt classifier. The confidence may additionally or alternatively be output with a calculated quantity. The cardiac flow area may be positioned in flow in a non-valvular region, such as based on positions of multiple heart valves. The models of the heart valves or a model including valve information indicates the position of the cardiac flow area relative to the valves. The cardiac flow area may be at a valve or located in a non-valvular region, such as 3 or more mm from a valve.

The image processor 12 is configured to calculate the cardiac flow from the Doppler flow data for the cardiac flow region or area. The calculation may be for a time or over time. The calculation may be for different or separate cardiac flow regions. The calculation may be limited to a portion of a heart cycle or the same repeating portion of multiple heart cycles. The limitation is based on timing from the fit valve models, such as based on when the valve is open or closed.

The image processor 12 is configured to generate an image. The fit model, identified anatomy, measurement surface graphic, calculated quantity, and/or other information is used to generate and/or included in the image. The patient-specific scan data may be used for imaging. The image provides a visualization of the heart and/or other port of the cardiac system.

The display 16 is a device, such as a CRT, LCD, plasma, projector, printer, or other output device for showing an image. The display 16 displays an image. For example, the image is generated from the ultrasound data and includes a visualization of the detected valve (e.g., a fit model), highlighted cardiac flow area, and an indication of a value of the calculated cardiac flow. Separate flow, anatomy, detected valve, fit model, measurement region, and/or calculated quantity images may be generated. The display 16 generates a visualization of the valve and/or cardiac flow area with highlighting or graphics. The highlighting is color, brightness, or other modification. A sequence of images representing the information over time may be displayed. The image may include an indication of the confidence.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A system for detecting cardiac flow, the system comprising:
    an ultrasound scanner configured to scan a heart volume of a patient, the scan providing B-mode and Doppler flow data;
    an image processor configured to detect two or more heart valves over time in the B-mode data, fit a model of the two or more heart valves to the patient using the B-mode data and a machine-learnt classifier, determine, with the machine-learnt classifier, a confidence value indicating an accuracy of the detection of the two or more heart valves in the model, place a first sampling plane for a first heart valve of the two or more heart valves and a second sampling plane for a second heart valve of the two or more heart valves based on the model, and track the first and second sampling planes over time, the image processor further configured to calculate the cardiac flow from the Doppler flow data for the first and second sampling planes over time; and
    a display configured to generate a visualization of the model over time as fit to the B-mode data, highlight a cardiac flow area, and indicate a value of the calculated cardiac flow.

2. The system of claim 1 wherein placing is based, in part, on the confidence value.

3. The system of claim 1 wherein the display is configured to indicate the confidence value.

4. The system of claim 1 wherein the image processor is configured to limit the calculation of the cardiac flow to a portion of a heart cycle based on timing from the fit model.

5. The system of claim 1 wherein the image processor is configured to place the first sampling plane and the second sampling plane based on positions of the two or more heart valves.

6. The system of claim 1, wherein the first sampling plane is for the mitral annulus of the patient and the second sampling plane is for the left ventricle outflow tract of the patient.

7. The system of claim 6, wherein the image processor is configured to detect the two or more valves by detecting a location, orientation, and scale of each of the mitral annulus and the left ventricle outflow tract represented by the B-mode data.

8. The system of claim 1, wherein detecting comprises fitting morphological models of the two or more valves to the B-mode data.

9. The system of claim 1, wherein calculating comprises calculating the cardiac flow value for in-flow, out-flow, and/or stroke volume.

10. The system of claim 1, wherein placing comprises placing based on the confidence value.

11. The system of claim 1, wherein the first and second sampling planes are tracked using optical flow, boundary detection, and/or motion prior information.

12. The system of claim 1, wherein ultrasound scanner comprising a transducer that is positioned on a chest of a patient such that acoustic energy passes between ribs of the patient to scan the heart volume or portion of the heart volume.

13. A system for detecting cardiac flow, the system comprising:
    a transducer positioned on the chest of a patient such that acoustic energy passes between ribs of the patient to scan a heart or portion of the heart generating B-mode and Doppler flow data; and
    an image processor configured to detect two or more heart valves over time in the B-mode data, fit a model of the two or more heart valves to the patient using the B-mode data and a machine-learnt classifier, determine, with the machine-learnt classifier, a confidence value indicating an accuracy of the detection of the two or more heart valves in the model, place a first sampling plane for a first heart valve of the two or more heart valves and a second sampling plane for a second heart valve of the two or more heart valves based on the model, and track the first and second sampling planes over time, the image processor further configured to calculate the cardiac flow from the Doppler flow data for the first and second sampling planes over time.

14. The system of claim 13, further comprising:
    a display configured to generate a visualization of the model over time as fit to the B-mode data, highlight a cardiac flow area, and indicate a value of the calculated cardiac flow.

15. A system for detecting cardiac flow, the system comprising:
    an ultrasound scanner configured to scan a heart volume of a patient over at least a heart cycle to acquire one or more volumetric ultrasound scans including B-mode and Doppler flow data;
    an image processor configured to detect two or more heart valves over time from the B-mode data of the one or more volumetric ultrasound scans, wherein detecting comprises detecting with a machine-learnt classifier, the image processor configured to fit a patient specific valve model to the detected two or more heart valves, determine a confidence value indicating an accuracy of the detecting of the mitral annulus and the left ventricle outflow tract in the fit patient specific valve model two or more heart valves, wherein determining the confidence comprises determining the confidence with the machine-learnt classifier, place a first sampling plane for the mitral annulus and a second sampling plane for the left ventricle outflow tract one or more sampling planes based on the fit patient specific valve model two or more heart valves, track the one or more first and second sampling planes over time based on optical flow, boundary detection, and motion prior; calculate a cardiac flow value from flow data of the volumetric ultrasound scans for the one or more first and second sampling planes over time, the calculating of the cardiac flow value limited to avoid flow during a portion of a heart cycle, and output an image of the cardiac flow value, wherein the image indicates the confidence value for the one or more first and second sampling planes.

16. The system of claim 15, wherein placing is based, in part, on the confidence value.

17. The system of claim 15, further comprising:

a display configured to display the image and indicate the confidence value.

18. The system of claim 15, wherein the image processor is configured to limit the calculation of the cardiac flow to a portion of a heart cycle based on timing from the fit model.

19. The system of claim 15, wherein the image processor is configured to place the first sampling plane and the second sampling plane based on positions of the two or more heart valves.

20. The system of claim 15, wherein the image processor is configured to limit the calculation of the cardiac flow to a portion of the heart cycle based on timing from the first and second models fit over the heart cycle to the B-mode data.

\* \* \* \* \*